United States Patent
Chen et al.

(10) Patent No.: US 11,654,177 B2
(45) Date of Patent: May 23, 2023

(54) ALOE EXTRACT AND METHODS FOR PRODUCING THE SAME

(71) Applicant: DAZZEON BIOTECHNOLOGY CO., LTD., New Taipei (TW)

(72) Inventors: Thomas Chen, Taipei (TW); Chih-Sheng Hung, Taipei (TW); Lung-Yao Wang, Taipei (TW); Yi-Ru Chen, Taipei (TW)

(73) Assignee: DAZZEON BIOTECHNOLOGY CO., LTD., New Taipei (TW)

( * ) Notice: Subject to any disclaimer, the term of this patent is extended or adjusted under 35 U.S.C. 154(b) by 0 days.

(21) Appl. No.: 17/467,444

(22) Filed: Sep. 6, 2021

(65) Prior Publication Data

US 2022/0072080 A1 Mar. 10, 2022

(30) Foreign Application Priority Data

Sep. 8, 2020 (TW) ................... 109130748

(51) Int. Cl.
*A61K 36/886* (2006.01)

(52) U.S. Cl.
CPC ........ *A61K 36/886* (2013.01); *A61K 2236/15* (2013.01); *A61K 2236/331* (2013.01); *A61K 2236/333* (2013.01); *A61K 2236/39* (2013.01); *A61K 2236/51* (2013.01); *A61K 2236/53* (2013.01)

(58) Field of Classification Search
None
See application file for complete search history.

(56) References Cited

FOREIGN PATENT DOCUMENTS

| EP | 0 216 310 A2 | * | 4/1987 |
| KR | 960011516 | * | 8/1996 |

* cited by examiner

*Primary Examiner* — Susan Hoffman

(57) ABSTRACT

Disclosed herein is a method for preparing an aloe extract. The method comprises steps of, mincing a mesophyll of an *Aloe* in water; heating the minced mixture to 60-80° C.; filtering the mixture to produce a first filtrate; drying the first filtrate; reconstituting the dried first filtrate in water; subjecting the first filtrate or the reconstituent to column chromatography and eluting the column with a first polar solvent; concentrating the eluent; purifying the concentrate with active carbons; filtering the purified concentrate to produce a second filtrate; concentrating the second filtrate; and adding a second polar solvent to the concentrated second filtrate thereby producing the aloe extract. The present disclosure also encompasses the aloe extract prepared by the present method. Said aloe extract has desired contents of O-acetyl groups or polysaccharides, and is useful for manufacturing food, pharmaceutical, or cosmetic products.

11 Claims, 4 Drawing Sheets

ALOE EXTRACT AND METHODS FOR PRODUCING THE SAME

CROSS-REFERENCE OF RELATED APPLICATION

This application claims priority to TW Application No. 109130748, filed on Sep. 8, 2020. The content of which application is incorporated herein by reference in its entirety.

BACKGROUND OF THE INVENTION

1. Field of the Invention

The present disclosure is related to a method for preparing an extract from an aloe mesophyll, particularly to an improved method for producing an aloe extract, and acemannan therefrom.

2. Description of Related Art

*Aloe* is a perennial herbaceous succulent plant of Asphodelaceae with a high medicinal value, and has been widely used as a folk medicine since ancient times. The medicinal effects of aloe are also detailed in the traditional Chinese pharmacopoeias such as "The Divine Husbandman's Herbal Foundation Canon" and "Herbal Foundation Compendium." Modern pharmacological research indicates that aloe has a wide range of pharmacological activities, such as soothing, moisturizing, anti-infective (for example, anti-fungus, anti-bacteria and anti-virus), anti-inflammatory, anti-itching, etc., which makes it suitable for use in treating burns and scalds and promoting wound healing, while eating aloe may help lower blood sugar, blood cholesterol, battle gastric ulcers, protect liver, remit constipation, promote immunity, treat cancer, and the like.

Acemannan is one of the important medicinal active ingredients of *aloe*, which endows aloe with the above-mentioned effects. Especially in terms of immune regulation and antiviral effects, acemannan may stimulate macrophage to secrete interferon (IFN), tumor necrosis factor-α (TNF-α), interleukin-1 (IL-1), etc., and combat viral infections via the immune responses associated with those cytokines. It is worth mentioning that reports have shown that acemannan is able to inhibit viral replication in individuals infected with human immunodeficiency virus (HIV), which in turns may considerably contribute to the treatment of acquired immune deficiency syndrome (AIDS).

Therefore, it is of great economic value for the development of an effective method for extracting acemannan. Acemannan is present in the water-soluble extract of *aloe*, and may be extracted via use of manifold methods. Nevertheless, such extraction methods are basically of laboratory grade, and the yield of acemannan is too low. In the method for industrial grade production, acemannan prepared therefrom is crude, with the concentration of acemannan being far from satisfaction. For example, the conventional method in general can only produce about 1 kg of acemannan crude extract from 100-200 kg of aloe mesophyll. In addition, the acemannan produced by these extraction methods is usually of poor quality, such as easy to become damp, agglomerated, unstable, yellowish in color, water immiscible, etc., resulting in the need for additional refining processes to improve the quality of acemannan, which in turns leads to higher manufacturing costs.

In view of the foregoing, there exists in the related art a need for an improved method for extracting acemannan with minimum-loss and high-quality, and is applicable to industrial-grade manufacturing processes, so that acemannan of improved quality may be economically and efficiently extracted from the raw material.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the present disclosure is directed to a method for preparing an aloe extract, which comprises:

(a) mincing a mesophyll of an *Aloe* in water;
(b) heating the minced mixture of the step (a) to 60-80° C.;
(c) filtering the mixture of the step (b) to produce a first filtrate;
(d) drying the first filtrate of the step (c);
(e) reconstituting the dried first filtrate of the step (d) in water;
(f) subjecting the first filtrate of the step (c) or the reconstituent of the step (e) to column chromatography and eluting the column packed with non-polar resins therein with a first polar solvent;
(g) concentrating the eluent of the step (f);
(h) purifying the concentrate of the step (g) with active carbons;
(i) filtering the purified concentrate of the step (h) to produce a second filtrate thereof;
(j) concentrating the second filtrate of the step (i); and
(k) adding a second polar solvent to the concentrated second filtrate of the step (j) thereby producing the aloe extract;

wherein the aloe extract has a level of O-acetyl groups above 200,000 mg/kg, a level of polysaccharides above 100,000 mg/kg; or a water solubility of at least 10 mg/ml.

According to other preferred embodiments of the present disclosure, the present method further comprises, prior to the step (d), steps of:

(c-1) repeating the steps (a) and (b) at least once;
(c-2) filtering the mixture of the step (c-1) to produce a filtrate thereof; and
(c-3) combining the respective filtrates of the steps (c) and (c-2).

According to still other preferred embodiments of the present disclosure, the present disclosure method further comprises steps of:

(l) reconstituting the aloe extract of the step (k) in the first polar solvent; and
(m) drying the reconstituent of the step (l).

According to one preferred embodiment of the present disclosure, the steps (c) or (i) is performed with an aid of a 60-120 or 200-350 mesh sieve or diatomite.

According to some embodiments of the present disclosure, said column chromatography is selected from the group consisting of affinity chromatography, supercritical fluid chromatography, ion exchange chromatography, size-exclusion chromatography, and expanded bed chromatographic adsorption. In one working example of the present disclosure, the column chromatography is the expanded bed chromatographic adsorption using an adsorption resin column.

According to some embodiments of the present disclosure, said column is made of non-polar resin. According to some embodiments of the present disclosure, said resin of the column has an average pore diameter of 25-50 nanometers.

According to some embodiments of the present disclosure, wherein the first polar solvent is water, <20% (volume %) $C_1$-$C_4$ alcohol or <20% (volume %) acetone; and the second polar solvent is 50-95% (volume %) $C_1$-$C_4$ alcohol or 50-95% (volume %) acetone. In one specified embodiment, said first and said second polar solvents are respectively 20% (volume %) ethanol and 85% (volume %) ethanol.

According to some embodiments of the present disclosure, the steps (g) and (j) are respectively achieved by evaporative concentration, freeze concentration, vacuum concentration, or membrane concentration.

According to some embodiments of the present disclosure, the step (g) is achieved by:
  (g-1) drying the eluent of the step (f); and
  (g-2) reconstituting the product of the step (g-1) in the first polar solvent.

According to some embodiments of the present disclosure, the *Aloe* is *Aloe africana, Aloe arborescens, Aloe chinensis* Baker, *Aloe ferox* Mill, *Aloe humilis* (L.) Mill. var. *echinata* (Willd.) Baker, *Aloe perryi, Aloe saponaria, Aloe spicata*, or *Aloe vera*. In one specified embodiment, the aloe is *Aloe vera*.

Another aspect of the present disclosure pertains to a water-soluble aloe extract prepared by the foregoing extraction method, and the aloe extract has a level of O-acetyl groups above 200,000 mg/kg, a level of polysaccharides above 100,000 mg/kg; or a water solubility of at least 10 mg/ml.

Many of the attendant features and advantages of the present disclosure will becomes better understood with reference to the following detailed description considered in connection with the accompanying drawings.

BRIEF DESCRIPTION OF THE DRAWINGS

These and other features, aspects and advantages of the present invention will become better understood with reference to the following description, appended claims and the accompanying drawings, where:

DESCRIPTION

Figure 1:
FIG. 1 is a photograph showing the appearance differences between the dried aloe extract prepared by the present method (Test sample A) and another two commercially available aloe extracts (Reference samples 1 and 2) in accordance with one embodiment of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a," "an," and "the" include the plural reference unless the context clearly dictates otherwise. Also, as used herein and in the claims, the terms "at least one" and "one or more" have the same meaning and include one, two, three, or more. Furthermore, the phrases "at least one of A, B, and C," "at least one of A, B, or C," and "at least one of A, B, and/or C," as use throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

As used herein, the term "fresh" refers to plant components that have not (yet) been processed, or only minimally processed (e.g., cut or sliced, packaged, and/or peeled) after harvest, and which are not preserved by substantive drying. Furthermore, the term "fresh" does not necessarily correlate with the time when the plants are harvested. Rather, it is used solely to differentiate parts of plants that have or have not being dried.

As used herein, the term "dry or dried" refers to the moisture level of a plant component after being dehydrated; moisture levels in dried plant components may range from 1 to 20% by weight, however, typical ranges are between 2 and 5%. The drying may carry out by any means known in the art, including natural drying (e.g., sun drying); kiln drying (or oven drying); hot air drying (e.g., cabinet drying, tunnel drying, belt drying, rotary drying, pneumatic drying, and fluidized bed drying); spray-drying; film drying (or drum drying); vacuum drying; freeze-drying (e.g., freeze-drying with vacuum, and freeze-drying without vacuum); puff drying, and the like.

The term "aloe extract" and other similar terms as used herein, refer to a composition prepared by contacting plant components from the aloe (including, without limitation, *Aloe africana, Aloe arborescens, Aloe chinensis* Baker, *Aloe ferox* Mill, *Aloe humilis* (L.) Mill. var. *echinata* (Willd.) Baker, *Aloe perryi, Aloe saponaria, Aloe spicata*, and *Aloe vera*) with a solvent following the procedures as described in the present method. It will be appreciated that the term encompasses crude extracts as well as processed or refined extracts. Specifically, crude extracts are prepared by a simple extraction, where part of the aloe (e.g., aloe mesophyll) is brought into contact with at least one extraction solvent, which may be a polar solvent or a non-polar solvent, depending on the nature of the target component to be extracted. Optionally, processed or refined extracts are produced by subjecting the crude extract to one or more separation and/or purification steps. The plant extract may be in liquid form, such as a solution, concentrate, or distillate; or it may be in solid form in which the solvent is removed, such as in paste, granulate or powder form.

II. Description of the Invention

The objective of the present disclosure is to provide a method for preparing a water-soluble aloe extract. The method is based at least in part on the discovery that extracting aloe by adsorption resins with specific properties (e.g., polar/non-polar, specific surface area, average pore size, etc.) under specific elution conditions (e.g., eluent type, concentration, pH value, flow rate, etc.) may produce an aloe extract characterized in having an improved level of acemannan. The present method is relatively simple and cost effective, and is suitable for applications in large-scale industrial production of aloe extract.

1. Methods for Preparing the *Aloe* Extract

One aspect of the present disclosure is to provide a method for preparing an aloe extract, in which the method comprises:

(a) mincing a mesophyll of an *Aloe* in water;
(b) heating the minced mixture of the step (a);
(c) filtering the mixture of the step (b) to produce a first filtrate;
(d) subjecting the first filtrate of the step (c) to column chromatography and eluting the column packed with non-polar resins therein with a first polar solvent;
(e) concentrating the eluent of the step (d);
(f) purifying the concentrate of the step (e) with active carbons;
(g) filtering the purified concentrate of the step (f) to produce a second filtrate thereof;
(h) concentrating the second filtrate of the step (g); and
(i) adding a second polar solvent to the concentrated second filtrate of the step (h) thereby producing the aloe extract;

wherein the aloe extract has a level of O-acetyl groups above 200,000 mg/kg, a level of polysaccharides above 100,000 mg/kg; or a water solubility of at least 10 mg/ml.

To produce the present aloe extract, fresh aloe leaves are harvested and used as raw materials, for example, in the present working Example 1, 500 kg of aloe mesophyll is used, in which the aloe leaves may undergo pre-processing (such as, cutting, peeling, and etc. at the minimal level) before being used in the present method, or may be directly used in the present method without pre-processing. The aloe suitable for use in the present method is as described above. In certain embodiments, the aloe is *Aloe vera*. To start the extraction, the aloe (e.g., *Aloe vera*) mesophyll is mixed with pure water (i.e., the first polar solvent) and grounded in a mixer to produce a minced mixture (the step (a)). Preferably, the amount of water may be 3 to 20 times more of the aloe mesophyll by weight, such as 3, 4, 5, 6, 7, 8, 9, 10, 11, 12, 13, 14, 15, 16, 17, 18, 19, or 20 times more of the aloe mesophyll by weight; more preferably, the amount of water may be 3 to 10 times more of the aloe mesophyll by weight, such as 3, 4, 5, 6, 7, 8, 9, or 10 times more of the aloe mesophyll by weight. According to the embodiments of the present disclosure, the amount of water is 5 times more of the aloe mesophyll by weight.

Then, the minced mixture of the step (a) is heated at 60-80° C. for one to three hours (the step (b)). Preferably, the minced mixture is heated to the temperature of 60, 61, 62, 63, 64, 65, 66, 67, 68, 69, 70, 71, 72, 73, 74, 75, 76, 77, 78, 79, or 80° C. for 1 to 3 hrs, such as 1, 1.5, 2, 2.5, or 3 hrs. Note that if the minced mixture is heated at a temperature lower than 60° C., it would lead to a lower yield of acemannan, by contrast, if the minced mixture is heated at a temperature above 80° C., it would cause degradation of acemannan. According to one preferred embodiment of the present disclosure, the minced mixture is heated at the temperature of 80° C. for 1 hour.

Then, the heated mixture of the step (b) is filtered, which may be achieved by any filtering means well known in the art (the step (c)), for example, by use of a sieve (e.g., 60-120 mesh or 200-350 mesh), diatomite, or the like, so as to produce a filtrate ("the first filtrate"). Alternatively, other methods may be adopted to remove impurities from the heated mixture of the step (c); such as membrane filtration, centrifugal separation, gravity sedimentation, and the like. According to one working example of the present disclosure, filtration is done by use of a 350 mesh sieve.

Optionally, after the step (c) and prior to proceeding to the step (d), steps (c-1) to (c-3) are performed. In the step (c-1), the steps (a) and (b) are repeated at least once (i.e., the step (a) is to mince aloe mesophyll in water, and the step (b) is to perform heat extraction of the mince of the step (a)); in the step (c-2), the extract of the step (c-1) is filtered; and in the step (c-3), the filtrate of the steps (c) and (c-2) are combined, so as to increase the amount of extract, and/or the yield. Furthermore, after the steps (c) or (c-3), the filtrate of the steps (c) or (c-3) may be dried via any known method, and the resulting dried product may be reconstituted in any suitable buffer or solution to give a reconstituent. According to one preferred embodiment of the present disclosure, said dried product is reconstituted in the first polar solvent (e.g., water).

In the step (d), the first filtrate of the step (c) or the reconstitution as described above is subjected to column chromatography. Examples of the column chromatography suitable for use in the present method include, but are not limited to, affinity chromatography, supercritical fluid chromatography, ion exchange chromatography, size-exclusion chromatography, and expanded bed chromatographic adsorption. According to one working example of the present disclosure, the column chromatography is performed by use of expanded bed chromatographic adsorption, in which the column is packed with adsorption resin.

The adsorption resin suitable for use in the present method may be: Strong polar resin (e.g., vinylpyridine series resin (GDX-401, Tianjin Chemical Reagent Two Factories), styrene divinylbenzene series resin (HPD-600, The Precious Grace Chemical Industry of Cang Zhou Co. Ltd.), vinylpyrrolidone series resin (PORAPAK™ S, Agilent), nitrogen oxides series resin (AmberLite™ XAD-11, XAD-12, Amberlite)); polar resin (e.g., phenol-formaldehyde series resin (AmberLite™ XAD-761, DuPont), nitrogen-containing polar compounds (GDX-501, Tianjin Chemical Reagent Two Factories), styrene series resin (HPD500/600, The Precious Grace Chemical Industry of Cang Zhou Co. Ltd.; NKA-II, Chemical Plant of Nankai Univ.), styrene nitrile series resin (NKA-9, Chemical Plant of Nankai Univ.), vinylpyrrolidone series resin (PORAPAK™ R, Agilent), cross-linked polystyrene series resin (S-8, Chemical Plant of Nankai Univ.), sulfoxide series resin (AmberLite™ XAD-9, DuPont), acrylamide series resin (AmberLite™ XAD-10, DuPont)); medium polar resin (e.g., styrene series resin (HPD400, HPD450, HPD600, The Precious Grace Chemical Industry of Cang Zhou Co. Ltd.), styrene divinylbenzene series resin (HPD-750, HPD826, The Precious Grace Chemical Industry of Cang Zhou Co. Ltd.), methacrylic series resin, styrene nitrile series resin (NKA-9, Chemical Plant of Nankai Univ.), acrylate series resin (AmberLite™ XAD-6, DuPont), a-methacrylate series resin (AmberLite™ XAD-7HP, XAD-8; DuPont)); weakly polar resin (e.g., styrene series resin (AB-8, Chemical Plant of Nankai Univ.; HPD450, HPD722, The Precious Grace Chemical Industry of Cang Zhou Co. Ltd.), acrylonitrile series resin (DA-201, Resin Branch Office of Tianjin Agricultural Chemicals Limited-Liability Co.), α-methyl styrene series resin (DM130, Chemical Plant of Nankai Univ.)); non-polar resin (e.g., styrene series resin (AmberLite™ XAD-1, XAD-2, XAD-3, XAD-4, XAD-5, XAD-1600, DuPont; D-101, Resin Branch Office of Tianjin Agricultural Chemicals Limited-Liability Co.; D3520, D4020, Chemical Plant of Nankai Univ.; GDX-104, GDX-105, Tianjin Chemical Reagent Two Factories; H-103, H-107, Chemical Plant of Nankai Univ.; HPD100, HPD100B, HPD300, HPD700, The Precious Grace Chemical Industry of Cang Zhou Co. Ltd.; SIP-1300, Shanghai Institute of Pharmaceutical Industry; X-5, Chemical Plant of Nankai Univ.), styrene divinylbenzene series resin (DIAION™ HP-20, Mitsubishi Chemical Corporation), a-methyl styrene series resin ($DM_2$, Chemical Plant of Nankai Univ.), a-methacrylate series resin). In one preferred embodiment, the adsorption resin suitable for use in the present extraction method is a non-polar resin (e.g., styrene divinylbenzene series resin (DIAION™ HP-20, Mitsubishi Chemical Corporation)).

The adsorption resin suitable for use in the present method has an average pore size between 0.1 and 150 nm, such as, 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, and 150 nm; preferably, the average pore size of the adsorption resin may be between 10 and 100 nm; more preferably, the average pore size of the adsorption resin may be between 25 and 50 nm. According to one preferred example of the present disclosure, the adsorption resin has an average pore size between 26 and 30 nm.

Prior to commencing column chromatography, the resins are activated, for example, by use of a second polar solvent (e.g., $C_1$-$C_4$ alcohol or acetone at the concentration of about 50-95% (volume %)). Examples of the $C_1$-$C_4$ alcohol suitable for activating the resins include, but are not limited to, methanol, ethanol, propanol, and tert-butanol. In one specific example, said $C_1$-$C_4$ alcohol is ethanol. According to embodiments of the present disclosure, said $C_1$-$C_4$ alcohols has a volume concentration about 50-95% (volume %), such as about 50, 55, 60, 65, 70, 75, 80, 85, 90, and 95% (volume %). According to one working example, the resins are activated by 95% (volume %) ethanol before being packed into a column, which is then eluted with water until no alcoholic smell is detected.

Then, in the step (d), the first filtrate of the step (c) or the above-mentioned reconstituent is loaded into the column, which is eluted with the first polar solvent (i.e., $C_1$-$C_4$ alcohol or acetone at the concentration of less than 20% (volume %)), the eluent is collected, in which the volume of the first polar solvent required for eluting the column is about 2-5 times of the volume of the resins. In one working example, the volume of the first polar solvent is about 2 times of the volume of the resins. According to the embodiments of the present disclosure, said $C_1$-$C_4$ alcohol is methanol, ethanol, propanol or tert-butanol. In one specific example, said $C_1$-$C_4$ alcohol is ethanol. In certain embodiments, said first polar solvent is water. In other embodiments, said $C_1$-$C_4$ alcohol is an alcohol solution having a volume concentration less than 20% (volume %), such as 0.1, 0.5, 1, 2, 3, 4, 5, 6, 7, 8, 9, 10, 11, 12, 13, 14, 15, 16, 17, 18, 19, and 20% (volume %). According to one working example, said first polar solvent is 20% (volume %) ethanol.

In step (e), the eluent of the step (d) is concentrated to give a concentrate of a first volume (hereinafter referred to as the first concentrate); the first volume is approximately equivalent to the volume of the resins. Said concentration may be achieved by any means well known in the art, for example, evaporative concentration, freeze concentration, vacuum concentration, and membrane concentration. Alternatively, the eluent of the step (d) may be dried and reconstituted in the first polar solvent (e.g., water) to give a reconstituent of the first volume (i.e., the first concentrate).

Then, in the step (f), a decoloring agent (preferably an active carbons) is added to the first concentrate or the reconstituent to remove pigments and/or small carbohydrates therefrom, thereby producing a white and bright aloe extract. Specifically, the first concentrate of the step (e) is purified with active carbons (the step (f)) to give a purified solution, in which the active carbons may be added in the amount of between about 1 and 20% (volume %), such as about 1, 2, 3, 4, 5, 6, 7, 8, 9, 10, 11, 12, 13, 14, 15, 16, 17, 18, 19, or 20% (volume %); preferably, the active carbons is added in the amount of between about 3 and 10% (volume %), such as about 3, 4, 5, 6, 7, 8, 9, or 10% (volume %). Or, other decoloring agents (e.g., zeolitic imidazolate framework materials, pulverized fuel ash, etc.) may also be used for decolorization in this step. The decolorizing agent (e.g., the active carbons) may subsequently be removed from the purified solution of the step (f) via any suitable means, so as to obtain a second filtrate (the step (g)).

Then, in the step (h), the second filtrate of the step (g) is concentrated, so as to enhance precipitation of the subsequent product in the step (i). That is, prior to the step (i), concentrating the second filtrate of the step (g) to produce a concentrate of a second volume (hereinafter referred to as the second concentrate), in which said second volume is about 0.1-0.5 times the first volume. In one working example, said second volume is about 0.5 times more of the first volume.

In the step (i), a second polar solvent is added to the second concentrate of the step (h), thereby producing the aloe extract; said second polar solvent may be any one of the polar solvent described above. In a further embodiment, to increase the amount of the precipitate, the mixture (i.e., the second polar solvent and the first or second concentrate) may be subjected to centrifugation, which may be any one of a continuous centrifuge, a decanter centrifuge, a solid-liquid separation centrifuge, and etc.

Optionally, the present method may further comprise steps of:

(j) reconstituting the aloe extract of the step (i) in the first polar solvent; and (k) drying the reconstituent of the step (j).

Examples of the first polar solvent and the drying method are as described above, and are not repeated here for the sake of brevity.

Accordingly, the present disclosure also encompasses a water-soluble *aloe* extract, which is prepared by the method described above, and the aloe extract thus produced is characterized in having a level of O-acetyl groups of at least 200,000 mg/kg, such as at least 200,000, 210,000, 220,000, 230,000, 240,000, 250,000, 200,000, 260,000, 270,000, 280,000, 290,000, 300,000, 310,000, 320,000, 330,000, 340,000, 350,000, 300,000, 360,000, 370,000, 380,000, 390,000, 400,000 mg/kg or more; and/or a level of polysaccharides of at least 100,000 mg/kg, such as at least 100,000, 110,000, 120,000, 130,000, 140,000, 150,000, 160,000, 170,000, 180,000, 190,000, 200,000, 210,000, 220,000, 230,000, 240,000, 250,000, 260,000, 270,000, 280,000, 290,000, 300,000, 310,000, 320,000, 330,000, 340,000, 350,000, 360,000, 370,000, 380,000, 390,000, 400,000 mg/kg or more; and/or a water solubility of at least 10 mg/ml, such as at least 10, 20, 30, 40, 50, 60, 70, 80, 90, 100, 150, 200, 250, 300, 350, 400, 450, 500 mg/ml or more.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Materials and Methods

1. Measurement of the O-Acetyl Group Level

A serial of standard acetylcholine chloride solutions and samples (i.e., the references and the test samples respectively at 10 mg/ml) were prepared. To measure the level of O-acetyl groups, 1 ml of the standard or the sample were mixed thoroughly with 2 ml of freshly prepared alkaline hydroxylamine solution (by mixing equal volumes of hydroxylamine hydrochloride solution (2M) with sodium hydroxide solution (3.5M)), and the mixture was let standing at room temperature for 4 minutes. After that, 1 ml of 4M hydrochloric acid and 1 ml of 0.37M ferric oxide-hydrochloric acid solution were added into the mixture and mixed thoroughly. The absorbance at 540 nm was measured via use of a spectrophotometer. A standard curve was constructed based on the 540 nm absorbance of the standards at various concentrations, and the level of O-acetyl groups (mg/kg) in the sample was calculated by interpolating the standard curve.

2. Measurement of the Polysaccharide Level

A serial of standard mannose solutions and samples (i.e., the references and the test samples respectively at 10 mg/ml) were prepared. For sample pretreatment, 1 ml of the sample solution was mixed with 9 ml of 95% alcohol, and the mixture was let standing overnight at 4° C., and then centrifuged. The precipitate was collected and reconstituted in 2 ml of water. To measure the polysaccharides, the standards and the pretreated samples were mixed thoroughly with 1 ml of 5% phenol, then 5 ml of 95% concentrated sulfuric acid was quickly dropped into the reaction mixture; which was thoroughly mixed and then let standing until it cooled down to room temperature. The absorbance of 490 nm was measured via use of a spectrophotometer. A standard curve was constructed based on the 490 nm absorbance obtained at various concentrations of the standards, and the level of polysaccharides (mg/kg) in the samples was calculated by interpolating from the standard curve.

3. Colorimetric Determination

Colorimetric detection of each samples (the reference or the test samples) was performed with a colorimeter (Spectrophotometer CM-700d, KONICA MINOLTA), where standard white was served as the detection standard. The L*, a*, b* values were respectively recorded after colorimetric analysis, in which the L* value refers to the black-white value, and the greater the value, the whiter the color, whereas the smaller the value, the darker the color; the a* value refers to the red-green value, and the greater the value, the redder the color, whereas the smaller the value, the greener the color; the b* value refers to the yellow-blue value, and the greater the value, the yellower the color, whereas the smaller the value, the bluer the color.

4. Determination of Hygroscopicity and Moisture Level

One gram of the sample (the reference or the test samples) was let standing indoors (at room temperature with humidity of about 66.8%) for more than 12 hours, before being subjected to the analysis of moisture content prior to (0 hours), and after being let standing for 12 hrs by use of an infrared moisture meter.

5. Determination of Water Solubility

One hundred mg of the sample (the reference or the test samples) were mixed thoroughly with 10 ml of reverse osmotic (RO) water, and the mixture was let standing at room temperature for 15 hours. Then, the dissolution of the samples was observed and recorded.

6. O-Acetyl Group Analysis

To analyze O-acetyl group by Fourier-transformed infrared spectroscopy, 5 mg of the sample (the reference or the test samples) was grinded with 100 mg of potassium bromide (KBr) in a mortar. About 60 mg of the grinded mixture was used to make a diaphragm, which was then scanned and analyzed by a Fourier-transformed infrared spectrometer (Perkin Elmer/Spectrum Two).

To analyze O-acetyl group by nuclear magnetic resonance (NMR), 20 mg of the sample (the reference or the test samples) was dissolved in 0.6 ml of heavy water ($D_2O$), and then the sample solution was scanned and analyzed with a nuclear magnetic resonance spectrometer (Bruker Avance III 600 MHz) at a frequency of 600 MHz.

7. Acemannan Analysis

The level of acemannan was determined by high-performance liquid chromatography (HPLC), a type of gel permeation chromatography (GPC). 30 mg of the sample (the reference or the test samples) was dissolved in 1 ml of water, and analyzed with HPLC (Agilent 1100) under the experimental condition of: Column: Waters column-Ultrahydrogel 1000 (7.8 mm×300 mm); flow rate: 1 ml/min; temperature: 40° C.; detector: a reflective index detector.

Example 1 Preparation of the Water-Soluble Aloe Extract

In this example, water-soluble aloe extract was prepared. Fresh aloe mesophyll (about 500 kg) were minced, mixed with pure water in a weight to volume ratio of 1:5 (about 2,500 liters of pure water), and blended in a blender. The minced mixture was heated to 80° C. for one hour, and the crude extract was filtered with a sieve of 350 mesh. The steps of the mincing fresh aloe mesophyll, mixing with water (about 2500 liters), heating (80° C. for one hour) and filtering were repeat once, and the two filtered extracts were combined and dried to produce a powder (about 5 kg). The powder was mixed with pure water in a weight to volume ratio of 1:12 (about 60 liters of pure water), the insoluble impurities therein were filtered out with a 350-mesh sieve, and the filtrate was kept for later use. The macroporous adsorption resins (model HP-20, 60 L) intended to be used in column chromatography was activated by 95% ethanol, and then were packed into a column about 100 L in volume. The column was eluted with pure water until the eluent was free of alcoholic smell.

The above-mentioned aloe filtrate (about 60 liters) was then loaded into the column containing the activated HP-20 resin (about 60 liters), and eluted with 120 liters of RO water or ethanol (<20% (volume %)) (approximately equivalent to twice the volume of the resins), and the eluent was then collected. The eluent was concentrated to a volume of about 60 liters (approximately equivalent to the volume of the resins), by vacuum concentration, freeze-drying or spray-drying to remove most of the liquid therein, and then the resulting product was reconstituted in water to a volume of about 60 liters. Then, for decolorization, the concentrate was mixed with 5% (volume %) active carbons to remove pigments and small molecular carbohydrates therein, and the entire mixture was then filtered with a 350 mesh sieve, followed by filtering with diatomite.

The filtrate was concentrated by vacuum concentration to a volume of about 30 liters (about 0.5 times the column volume), and then precipitated with ethanol, in which ethanol was added into the concentrate and adjusted to a concentration of 85% (volume %). The thus produced precipitate was centrifuged, the pellet was reconstituted in water, and the reconstituent was freeze-dried or spray-dried to give the final *aloe* extract (about 1 kg).

Example 2 Characterization of the Water-Soluble *Aloe* Extract of Example 1

In this example, the aloe extract of Example 1 was analyzed to determine its levels of O-acetyl groups and polysaccharides, and other properties such as color, appearance, and hygroscopicity.

2.1 the O-Acetyl Group Level

The O-acetyl group levels in the aloe extract of Example 1 (i.e., test samples) and the commercial samples were determined in accordance with the process described in "Materials and Methods". The results are summarized in Table 1.

TABLE 1

| The O-acetyl group level in each samples | |
|---|---|
| Sample name | The O-acetyl group level (mg/kg) |
| Aloe mesophyll | <1,000 |
| Test sample A | 273, 510 |
| Test sample B | 287, 040 |
| Test sample C | 294, 690 |
| Reference sample 1 | 83, 940 |
| Reference sample 2 | 71, 620 |

According to the results in Table 1 above, the O-acetyl group level in the *aloe* extracts of Example 1 (Test samples A to C) was 285,080 mg/kg on average, which was about 3.6 times of that of the commercially available aloe extracts (Reference samples 1 and 2, (77,780 mg/kg on average), which indicated that the method described in Example 1 can produce an aloe extract with a relatively higher amount of the O-acetyl groups.

2.2 the Polysaccharide Level

The polysaccharide level in each samples was determined in accordance with the process described in "Materials and methods," and the results are summarized in Table 2.

TABLE 2

| The polysaccharide level in each samples | |
|---|---|
| Sample name | The polysaccharide level (mg/kg) |
| Aloe mesophyll | <1,000 |
| Test sample A | 215, 763 |
| Test sample B | 201, 702 |
| Test sample C | 232, 586 |
| Reference sample 1 | 79, 733 |
| Reference sample 2 | 86, 767 |

According to Table 2, the polysaccharide level in the aloe extracts of Example 1 (Test samples A to C) was 216,684 mg/kg on average, which was about 2.6 times of that of the commercially available aloe extracts (References samples 1 and 2; 83,250 mg/kg on average), which indicated that the method described in Example 1 can produce an aloe extract with a relatively higher amount of the polysaccharides.

2.3 Appearance and Color

The differences in appearance between the aloe extract of Example 1 (Test sample A) and the commercially available aloe extracts (Reference samples 1 and 2) was shown in the photo of FIG. 1. To distinguish the color between the test and reference samples, a colorimeter was further used to compare the color, with standard white as the comparison benchmark. The results are summarized in Table 3.

TABLE 3

The colorimetric results of each samples

| Sample name | The L* value | The a* value | The b* value |
| --- | --- | --- | --- |
| Aloe mesophyll | 99.41 | −0.17 | −0.05 |
| Test sample A | 89.48 | −0.89 | 3.35 |
| Test sample B | 89.66 | −0.84 | 3.50 |
| Test sample C | 90.23 | −0.74 | 5.36 |
| Reference sample 1 | 82.18 | 3.16 | 20.57 |
| Reference sample 2 | 81.71 | 3.15 | 20.49 |

According to Table 3, the standard white had the L* value of about 100, and the a* value and b* value of almost zero. Based on this, the aloe extracts of Example 1 (Test samples A to C) (with an average L* value of 89.79, an average a* value of −0.82, and an average b* value of 4.07, all of which were close to the values of the standard white) were substantially a white powder in appearance, whereas the commercially available aloe extracts (Reference samples 1 and 2) (with an average L* value of 81.95, an average a* value of 3.16, and an average b* value of 20.53) were substantially a yellow powder.

2.4 Hygroscopicity and Moisture Level

Figure 2:
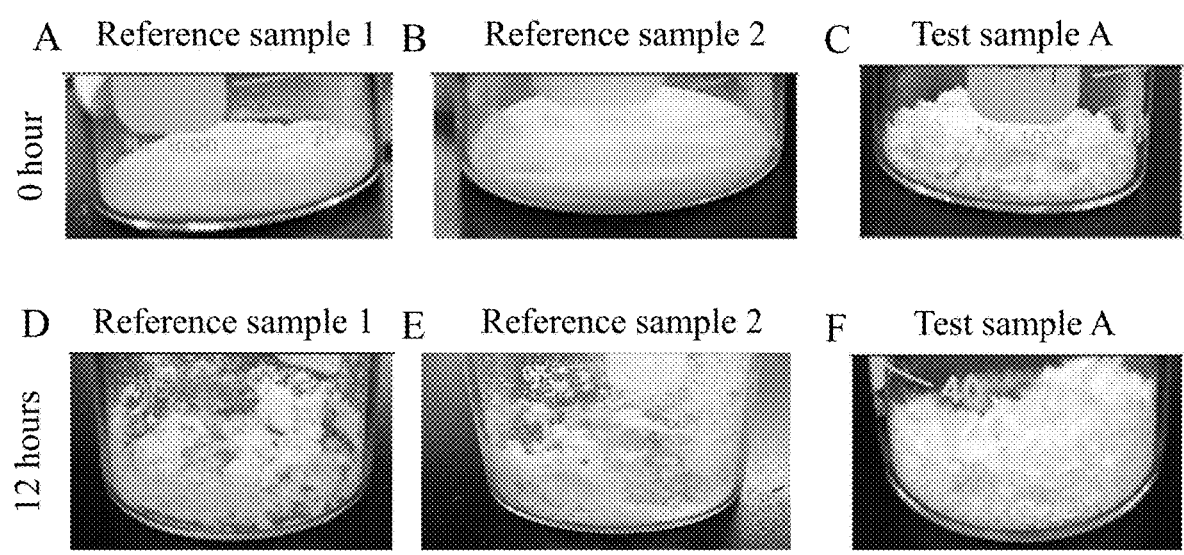
FIG. 2 are photographs showing the hygroscopicity of the dried aloe extract produced by the present method (Test sample A) and that of the commercially available aloe extracts (Reference samples 1 and 2) in accordance with one embodiment of the present disclosure, in which panels A to C are photos of aloe extract samples before standing (0 hours), while panels D to F are photos of aloe extract samples after being left standing for 12 hours.

Reference is made to FIG. 2, which illustrates the hygroscopicity of the *aloe* extract of Example 1 (Test sample A) and the commercially available aloe extracts (Reference samples 1 and 2). All three samples were in the form of dry powders before the test (FIG. 2, panels A-C). During the test, the powders of Reference samples 1 and 2 had aggregated into agglomerates after being let standing for about 30 minutes; and the powders adhered to the wall of the test tube after being let standing for about 1 hour. In the meanwhile, the powder of Test sample A showed no sign of stickiness and remained dispersed (data not shown). The changes in appearance of the three samples were observed after 12 hours, and relatively large amounts of the powders of Reference samples 1 and 2 were found to adhere to the wall of the test tube (FIG. 2, panels D-E), whereas the powder of Test sample A remained unadhered and dispersed (FIG. 2, panel F). Then, the changes in moisture content of those samples before and after standing were further determined with an infrared moisture meter, and the changes in moisture content of References 1 and 2 (increased by 8.505% and 9.172%, respectively) were both about twice higher than that of Test sample A (an increase of 4.945%). This result indicated that the aloe extract of Example 1 (Test sample A) was relatively more stable than the commercially available aloe extracts. Moreover, it is also expected that the stability of the aloe extract of Example 1 (Test sample A) can reach at least 6 months.

2.5 Water Solubility

Figure 3:
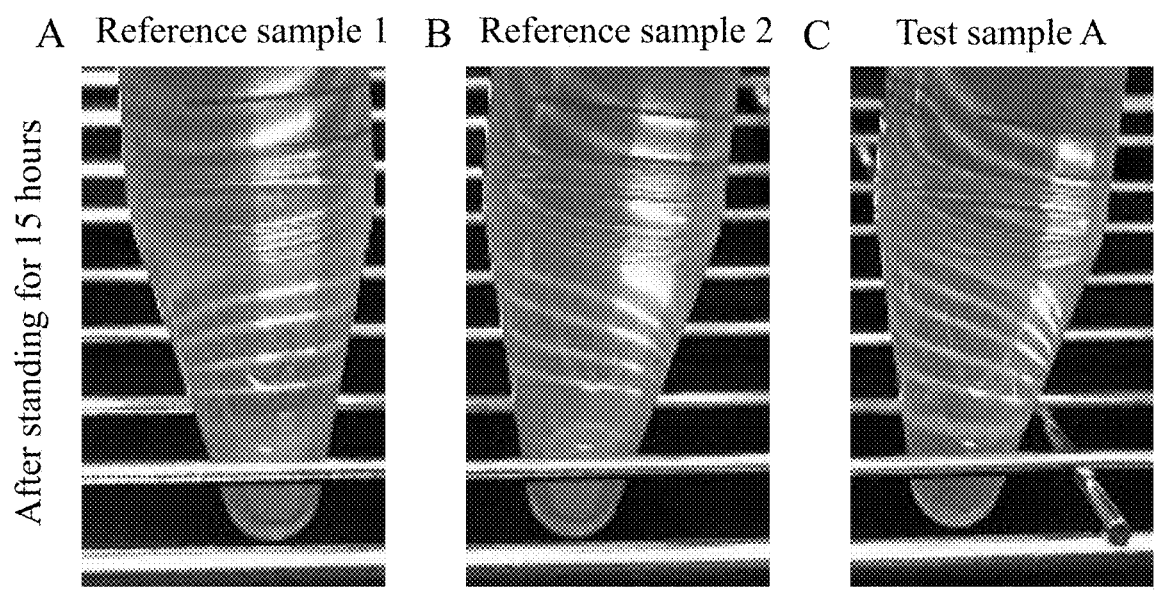
FIG. 3 are photographs depicting the water solubility of the aloe extract produced by the present method (Test sample A) and that of the commercially available aloe extracts (Reference samples 1 and 2) in accordance with one embodiment of the present disclosure, in which water solubility was measured after the aloe extract samples were dissolved in water and let standing for 15 hours.

The water solubility of the aloe extract of Example 1 (Test sample A) and the commercially available aloe extracts (Reference samples 1 and 2) were determined in this example, in which 100 mg of the samples were dissolved in 10 ml of RO water, and the results are depicted in FIG. 3. It was found that Reference samples 1 and 2 respectively dissolved in a slower rate, in which at least 50% of the sample remained in solid form at the bottom of the test tube even after being let standing at room temperature for more than 15 hours, and it took extra strong shaking of the test tube several times to completely dissolve the powders (FIG. 3, panels A-B). By contrast, Test sample A dissolved much faster, with all the powders completely dissolved in water in 30 minutes (24 minutes on average) (FIG. 3, panel C). Accordingly, the water solubility of the aloe extract of Example 1 (Test sample A) was determined to be at least 10 mg/ml. The results of this example evidenced that the water solubility of the *aloe* extract produced by the method of Example 1 was relatively high, easy to be adsorbed by human body, thereby increasing its bioavailability.

2.6 O-Acetyl Group Analysis

In this example, Fourier-transformed infrared spectroscopy (FT-IR) (FIG. 4) and nuclear magnetic resonance (NMR) (data not shown) were respectively used to identify the O-acetyl group in the aloe extract of Example 1 and the commercial *aloe* extracts. Results are provided in FIG. 4.

Figure 4:
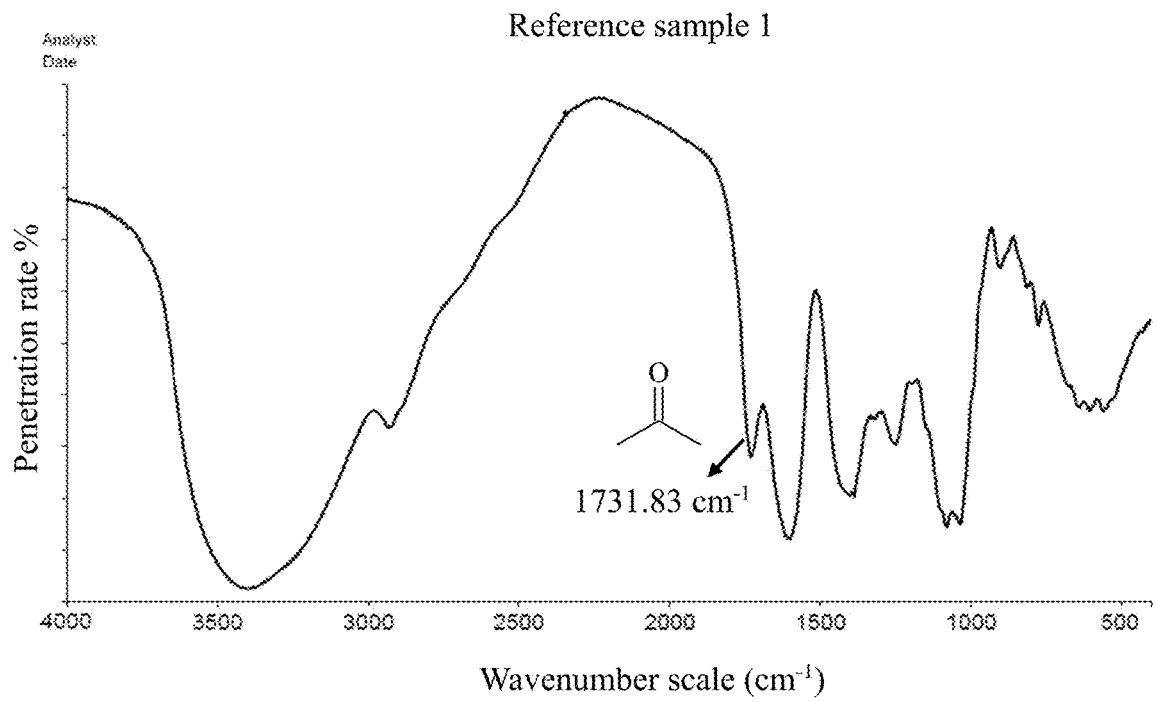
FIG. 4 depicts the Fourier-transformed infrared (FT-IR) analysis on the level of O-acetyl groups of (A) the commercially available aloe extract (Reference sample 1) and (B) the aloe extract produced by the present method (Test sample A).
Figure 4:
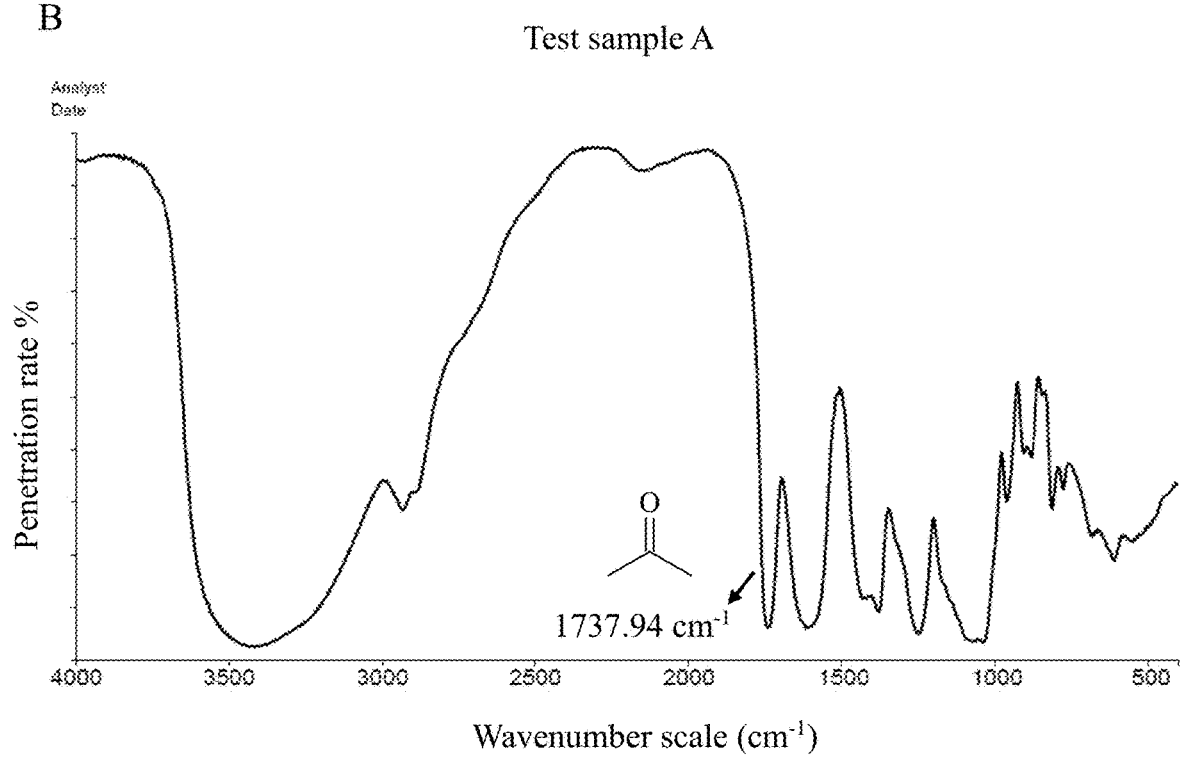

Reference is made to FIG. 4, panel A, in which the arrow at near 1,731.83 cm$^{-1}$ was where O-acetyl group-carbonyl (C=O) appeared in the Reference sample 1. The same functional group (1737.94 cm$^{-1}$) also appeared in the Test sample A (FIG. 4, panel B), suggesting that Test sample A and Reference sample 1 all possessed the same O-acetyl group.

According to $^1$H NMR (D$_2$O, 600 MHz) spectrums of Reference sample 1 and Test sample A, both samples all possessed the characteristic absorption signal of O-acetyl group near $\delta_H$ 2.13, also suggesting that Test sample A and Reference sample 1 all possessed the same O-acetyl group.

2.7 Acemannan Analysis

Figure 5:
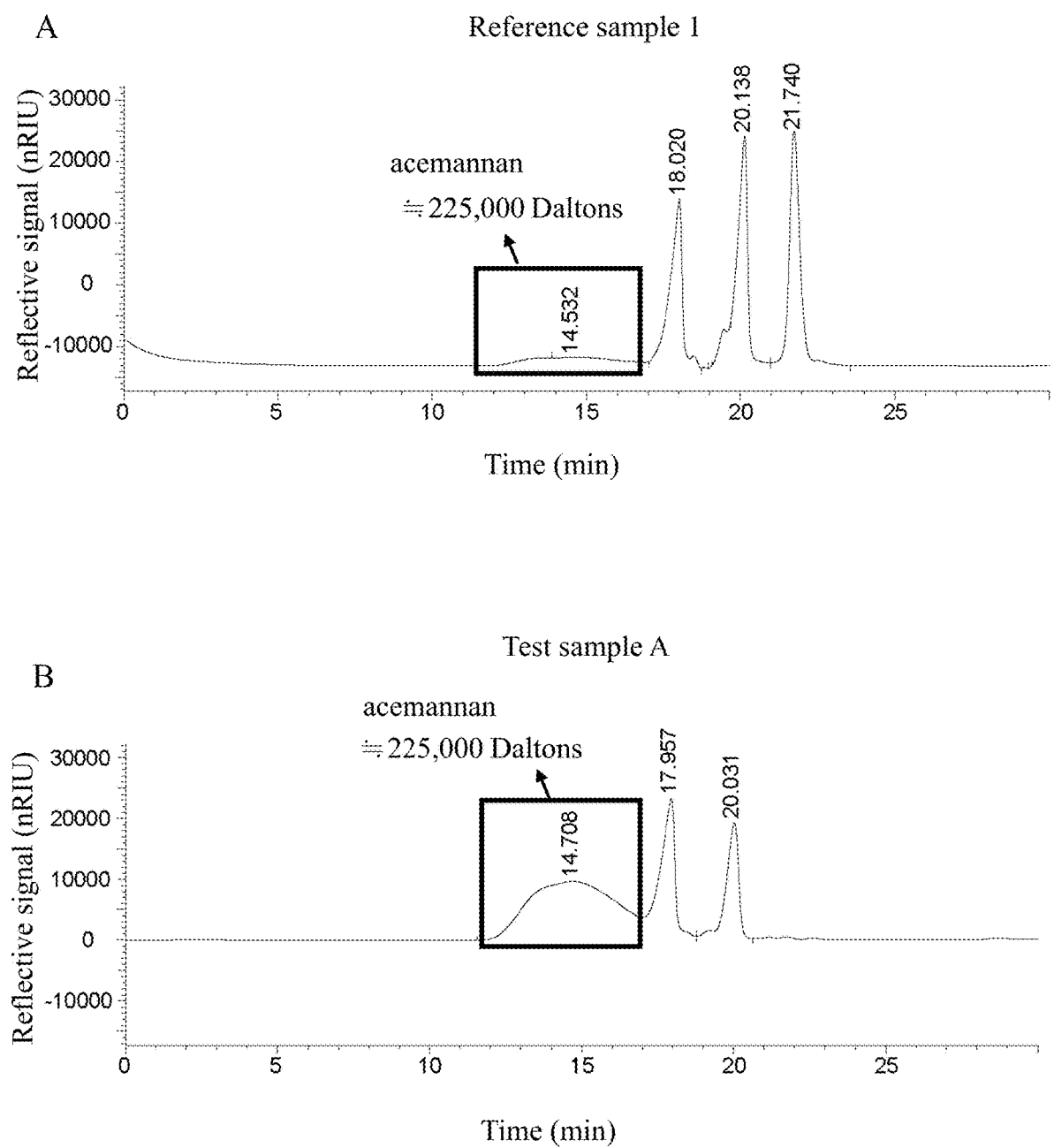
FIG. 5 depicts gel permeation chromatography (GPC) analysis on the level of acemannan in (A) the commercially available aloe extract (Reference sample 1) and (B) the aloe extract produced by the present method (Test sample A).

In this example, gel permeation chromatography (GPC) was used to analyze acemannan in the aloe extract of Example 1 and the commercially available aloe extract, and results are provided FIG. 5. Referring to FIG. 5, panel A, in which the molecular weight about 225,000 Daltons (Da) of acemanna in the Reference sample 1 was shown. The same molecular weight about 225,000 Da also appeared in the Test sample A, (FIG. 5, panel B), suggesting that Test sample A and Reference sample 1 all possessed the same acemannan molecule.

Taken together, for qualitative analysis of O-acetyl group (Example 2.6) and acemannan (Example 2.7), the aloe extract of Example 1 was similar to that of the commercially available aloe extracts, indicating that the two aloe extracts had similar composition. And in terms of the appearance and color, hygroscopicity and moisture level, and water solubility, the aloe extract of Example 1 was fairer in appearance, less absorptive in moisture (better stability), and higher water solubility, as compared to those of the commercially available aloe extracts.

In sum, the present disclosure presents a method suitable for industrial-grade preparation of aloe extract, and the water-soluble aloe extract prepared by the present method was better in quality (i.e., the product has a high degree of O-acetylation, good stability, less absorptive in moisture, and a higher water solubility), which eliminates the need for additional processing and refinement, and therefore high-quality water-soluble aloe extract may be obtained at an economic cost.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for preparing an aloe extract, comprising:
   (a) mincing a mesophyll of an *Aloe* in water;
   (b) heating the minced mixture of the step (a) to 60-80° C.;
   (c) filtering the mixture of the step (b) to produce a first filtrate;
   (d) drying the first filtrate of the step (c);
   (e) reconstituting the dried first filtrate of the step (d) in water;
   (f) subjecting the first filtrate of the step (c) or the reconstituent of the step (e) to column chromatography and eluting the column packed with non-polar resins therein with a first polar solvent;
   (g) concentrating the eluent of the step (f);
   (h) purifying the concentrate of the step (g) with active carbons;
   (i) filtering the purified concentrate of the step (h) to produce a second filtrate thereof;
   (j) concentrating the second filtrate of the step (i); and
   (k) adding a second polar solvent to the concentrated second filtrate of the step (j) thereby producing the aloe extract;
   wherein the aloe extract has a level of O-acetyl groups above 200,000 mg/kg, a level of polysaccharides above 100,000 mg/kg; or a water solubility of at least 10 mg/ml.

2. The method of claim 1, further comprising, prior to the step (d), steps of:
   (c-1) repeating the steps (a) and (b) at least once;
   (c-2) filtering the mixture of the step (c-1) to produce a filtrate thereof; and
   (c-3) combining the respective filtrates of the steps (c) and (c-2).

3. The method of claim 1, further comprising steps of:
   (l) reconstituting the aloe extract of the step (k) in the first polar solvent; and
   (m) drying the reconstituent of the step (l).

4. The method of claim 1, wherein the steps (c) or (i) is performed with an aid of a 60-120 or 200-350 mesh sieve or diatomite.

5. The method of claim 1, wherein the column chromatography is selected from the group consisting of affinity chromatography, supercritical fluid chromatography, ion exchange chromatography, size-exclusion chromatography, and expanded bed chromatographic adsorption.

6. The method of claim 5, wherein the expanded bed chromatographic adsorption uses an adsorption resin column.

7. The method of claim 1, wherein the first polar solvent is water, <20% (volume %) $C_1$-$C_4$ alcohol or <20% (volume %) acetone; and the second polar solvent is 50-95% (volume %) $C_1$-$C_4$ alcohol or 50-95% (volume %) acetone.

8. The method of claim 7, wherein the first and second polar solvents are respectively 20% (volume %) ethanol and 85% (volume %) ethanol.

9. The method of claim 1, wherein the steps (g) and (j) are respectively achieved by evaporative concentration, freeze concentration, vacuum concentration, or membrane concentration.

10. The method of claim 1, wherein the step (g) is achieved by:
    (g-1) drying the eluent of the step (f); and
    (g-2) reconstituting the product of the step (g-1) in the first polar solvent.

11. The method of claim 1, wherein the *Aloe* is *Aloe africana, Aloe arborescens, Aloe chinensis* Baker, *Aloe ferox* Mill, *Aloe humilis* (L.) Mill. var *echinata* (Willd.) Baker, *Aloe perryi, Aloe saponaria, Aloe spicata*, or *Aloe vera*.

* * * * *